United States Patent
Ghannam

(10) Patent No.: US 10,239,752 B2
(45) Date of Patent: Mar. 26, 2019

(54) SURFACE PLASMON-BASED NANOSENSORS AND SYSTEMS AND METHODS FOR SENSING PHOTONS AND CHEMICAL OR BIOLOGICAL AGENTS

(71) Applicant: KING SAUD UNIVERSITY, Riyadh (SA)

(72) Inventor: Talal Ghannam, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 446 days.

(21) Appl. No.: 14/168,051

(22) Filed: Jan. 30, 2014

(65) Prior Publication Data

US 2014/0285809 A1 Sep. 25, 2014
US 2015/0276596 A2 Oct. 1, 2015

(30) Foreign Application Priority Data

Mar. 19, 2013 (EP) ..................................... 13159918

(51) Int. Cl.
| | |
|---|---|
| *B82Y 15/00* | (2011.01) |
| *G01N 21/64* | (2006.01) |
| *G01N 21/552* | (2014.01) |
| *G01N 21/59* | (2006.01) |

(52) U.S. Cl.
CPC ........... *B82Y 15/00* (2013.01); *G01N 21/554* (2013.01); *G01N 21/648* (2013.01); *G01N 21/6489* (2013.01); *G01N 2021/5903* (2013.01)

(58) Field of Classification Search
CPC ............... G01N 21/554; G01N 21/648; G01N 21/6489; G01N 21/553; G01N 21/658; G01N 2021/5903; B82Y 15/00
See application file for complete search history.

(56) References Cited

U.S. PATENT DOCUMENTS

| | | | | |
|---|---|---|---|---|
| 6,815,064 B2 * | 11/2004 | Treadway | ............... | C09K 11/08 |
| | | | | 257/E33.004 |
| 7,449,299 B2 * | 11/2008 | Bauer | ................... | B82Y 15/00 |
| | | | | 435/17 |
| 8,197,756 B2 * | 6/2012 | Pison | ....................... | B82Y 5/00 |
| | | | | 422/68.1 |

(Continued)

OTHER PUBLICATIONS

Cox, Joel, D. et al., 2012, Dipole-dipole interaction between a quantum dot and a graphene nanodisk, Phys. Rev. B 86, 125452, pp. 1-11.*

(Continued)

*Primary Examiner* — Gordon J Stock, Jr.
(74) *Attorney, Agent, or Firm* — Renner, Otto, Boisselle & Sklar, LLP

(57) ABSTRACT

Surface plasmon-based nanosensor, comprising: at least one first element of metal, preferably silver or gold, or of semiconductor, the first element being excitable to surface Plasmon resonance, in particular localized surface plasmon resonance, in the presence of electromagnetic radiation from a source, and at least one second element preferably near the first element that in the presence of the electromagnetic radiation is exciton-plasmon coupled to the first element and emits electromagnetic radiation representative of the exciton-plasmon coupling, and systems and methods for sensing photons and chemical or biological agents.

3 Claims, 4 Drawing Sheets

(56) References Cited

U.S. PATENT DOCUMENTS

| | | | |
|---|---|---|---|
| 2004/0155184 A1 | 8/2004 | Stockman et al. | |
| 2006/0148104 A1* | 7/2006 | Marini | B82Y 5/00 436/524 |
| 2006/0183247 A1* | 8/2006 | Kim | A61K 49/0065 436/524 |
| 2009/0200486 A1* | 8/2009 | Wu | B82Y 5/00 250/461.1 |
| 2010/0264333 A1 | 10/2010 | Offermans et al. | |
| 2011/0170103 A1 | 7/2011 | Gomez Rivas et al. | |
| 2012/0107952 A1 | 5/2012 | Geddes et al. | |
| 2013/0148126 A1 | 6/2013 | Walters et al. | |
| 2014/0125976 A1* | 5/2014 | Kim | G01N 21/658 356/301 |
| 2014/0268128 A1* | 9/2014 | Wang | G01N 21/658 356/301 |

OTHER PUBLICATIONS

Biju, V. et al., 2008, Semiconductor quantum dots and metal nanoparticles: syntheses, optical properties, and biological applications, Anal Bioanal Chem 391: 2469-2495.*

Sadeghi, S.M., 2011, Plasmonic Metaresonance Nanosensors: Ultrasensitive Tunable Optical Sensors Based on Nanoparticle Molecules, IEEE Transactions on Nanotechnology, vol. 10, No. 3, pp. 566-571.*

Hatef, Ali et al., 2012, Quantum dot-metallic nanorod sensors via exciton-plasmon interaction, Nanotechnology 24, 8 pages.*

Achermann, Marc, "Exciton-Plasmon Interactions in Metal-Semiconductor Nanostructures," 2010, The Journal of Physical Chemistry Letters, 1, pp. 2837-2843.*

Viste, Pierre et al., "Enhancement and Quenching Regimes in Metal-Semiconductor Hybrid Optical Nanosources," 2010, ACS Nano, vol. 4, No. 2, pp. 759-764.*

Protsenko I E et al; "Dipole nano-laser", Journal of Physics: Conference Series, Institute of Physics Publishing, Bristol, GB, vol. 107. No. 1, Jan. 1, 2008, pp. 1-8.

Ghannam T; Dipole nano-laser: the effect of an external electric field; Journal of Physics B, Atomic Molecular and Optical Physics, Institute of Physics Publishing, Bristol, GB, vol. 43, No. 15, Jul. 20, 2010, pp. 1-5.

Ghannam T; "Coherent light emission from a nanosystem embedded within a polaritonic band-gap medium", Physical Review A (Atomic, Molecular, and Optical Physics), APS Through AIP USA, vol. 85, No. 3, Mar. 1, 2012, pp. 033803-1-033803-3.

EP13159918.5; Extended European Search Report dated Jul. 26, 2013.

* cited by examiner

SURFACE PLASMON-BASED NANOSENSORS AND SYSTEMS AND METHODS FOR SENSING PHOTONS AND CHEMICAL OR BIOLOGICAL AGENTS

CROSS-REFERENCE TO RELATED APPLICATION

The present application is related to and claims priority under 35 U.S.C. § 119 to European Application No. 13159918.5, filed 19 Mar. 2013, the entirety of which is hereby incorporated herein by reference.

TECHNICAL FIELD

The present invention relates to surface plasmon-based nanosensors, a system for sensing photons, a system for sensing chemical or biological agents, a method for sensing photons and a method for sensing chemical or biological agents.

BACKGROUND

Nano-scale systems have demonstrated many novel and interesting optical properties. These systems are extremely important for future photon-based devices among many other applications. One of the most important nano-devices are nanosensors.

SUMMARY

It is the object of the present invention to provide a nanosensor that is small, but yet sensitive to weak electromagnetic signals/fields or changes thereof.

This aim is achieved by a surface plasmon-based nanosensor, comprising: at least one first element of metal, preferably silver or gold, or of semiconductor, the first element being excitable to surface plasmon resonance, in particular localized surface Plasmon resonance, in the presence of electromagnetic radiation from a source, and at least one second element preferably near the first element that in the presence of the electromagnetic radiation is exiton-plasmon coupled to the first element and emits electromagnetic radiation representative of the exiton-plasmon coupling. Said nanosensor might be called "a plasmonic sensor" as well and can be categorized as an optical sensor. The at least one first element and the at least one second element are usually different.

According to further a further aspect, this aim is also achieved by a system for sensing photons of electromagnetic radiation from an external source, comprising: a surface plasmon-based nanosensor and a detector for detecting electromagnetic radiation emitted by the second element in response to electromagnetic radiation from an external source.

Further, according to further aspect the invention provides a system for sensing chemical or biological agents, comprising: a surface plasmon-based nanosensor, and a detector for detecting electromagnetic radiation emitted by the second element in response to the electromagnetic radiation from an external source or the internal source with a chemical or biological agent in direct or indirect contact with the at least one first element, in particular further comprising an evaluation unit for evaluating the identity of the chemical or biological agent based on the detected electromagnetic radiation.

This aim also achieved by a surface plasmon-based nanosensor, comprising: at least one first element of metal, preferably silver or gold, or of semiconductor, the first element being excitable to surface plasmon resonance, in particular localized surface plasmon resonance, in the presence of electromagnetic radiation from a source and at least one second element preferably near the first element for exciting surface plasmon resonance of the at least one first element.

The invention also provides a system for sensing photons of electromagnetic radiation from an external source, comprising: a surface plasmon-based nanosensor, a pumping unit for pumping the at least one second element and a detector for detecting the total electromagnetic radiation emitted by the at least first element and the at least one second element in response to electromagnetic radiation emitted by an external source or the internal source and incident on the at least one first element and the at least one second element, in particular further comprising an evaluation unit for evaluating the statistics, in particular the frequency and/or the intensity and/or photon number, of the electromagnetic radiation from the external source based on the detected electromagnetic radiation.

Further, this aim is achieved by a system for sensing chemical or biological agents, comprising: a surface plasmon-based nanosensor, a pumping unit for pumping the at least one second element and a detector for detecting the total electromagnetic radiation emitted by the at least one first element and the at least one second element in response to the electromagnetic radiation emitted by an external source or the internal source and incident on the at least one first element and the at least one second element with a chemical or biological agent in direct or indirect contact with the at least one first element.

The present invention is also directed to the use of a nanosensor or of a system for sensing photons and the use of a nanosensor or of a system for sensing chemical or biological agents.

The present invention also provides a method for sensing photons of electromagnetic radiation from a source, comprising: irradiating at least one first element of metal, preferably silver or gold, or of semiconductor, excitable to surface plasmon resonance, in particular localized surface plasmon resonance, with electromagnetic radiation from a source for exciting surface plasmon resonance on said at least one first element, providing for exciton-plasmon coupling between the at least one first element and at least one second element and for emission of electromagnetic radiation by the at least one second element, and detecting the electromagnetic radiation emitted by the at least one second element.

Also, the present invention provides a method for sensing photons of electromagnetic radiation from a source, comprising: irradiating at least one first element of metal, preferably silver or gold, or of semiconductor, excitable to surface plasmon resonance, in particular localized surface plasmon resonance, and at least one second element with electromagnetic radiation from a source, the at least one second element being pumped by pumping unit for exciting surface plasmon resonance on or in the at least first element and detecting the total electromagnetic radiation emitted by the exiton-plasmon coupled pumped at least one second element and at least one first element.

In addition, the present invention provides a method for sensing chemical or biological agents, comprising: directly or indirectly contacting at least one first element of metal, preferably silver or gold, or of semiconductor, excitable to surface plasmon resonance, in particular localized surface plasmon resonance, with a sample comprising a chemical or biological agent to be sensed, irradiating the at least one first element with electromagnetic radiation from an internal or external source for exciting surface plasmon resonance on said at least one first element, providing for exciton-plasmon coupling between the at least one first element and the at least one second element and for emission of electromagnetic radiation by the at least one second element, and detecting the electromagnetic radiation emitted by the at least one second element.

Finally, the present invention provides a method for sensing chemical or biological agents, comprising: directly or indirectly contacting at least one first element of metal, preferably silver or gold, or of semiconductor, excitable to surface plasmon resonance, in particular localized surface plasmon resonance, with a sample comprising a chemical or biological agent to be sensed, irradiating the at least one first element and the at least one second element with electromagnetic radiation from a source, the at least one second element being pumped by a pumping unit for exciting surface plasmon resonance on said at least one first element and detecting the total electromagnetic radiation emitted by the exciton-plasmon coupled pumped at least one second element and at least one first element.

According to a special embodiment of the nanosensor, the at least one first element is a nanoparticle and/or the at least one second element is quantum dot. More generally, the second element could be a two-level-system (TLS).

Preferably the at least one second element is preferably totally embedded in a matrix of Photonic or Polaritonic Band-gap (PGB)-material, preferably silicon carbide (SiC), and/or wherein the at least one first element is at least or only partially or totally embedded in a matrix of Photonic or Polaritonic Band-gap (PGB)-material, preferably silicon carbide (SiC).

A further special embodiment is characterized in further comprising an internal source capable of emitting the electromagnetic radiation. Such an embodiment would be well suited for use of the nanosensor as a bio-sensor for sensing biological or chemical agents (analytes).

Conveniently, the system comprises a shielding for shielding the at least one second element against external electromagnetic radiation.

According to a special embodiment of the nanosensor, the at least one first element is a nanoparticle and/or the at least one second element is a quantum dot. More generally, the at least one second element might be a two-level-system (TLS).

Preferably, the at least one second element is preferably totally embedded in a matrix of Photonic or Polaritonic Band-gap (PGB)-material, preferably silicon carbide (SiC), and/or wherein the at least one first element is at least or only partially or totally embedded in a matrix of Photonic or Polaritonic Band-gap (PGB)-material, preferably silicon carbide (SiC).

In particular when being used as a biological sensor (bio-sensor) or chemical sensor, it might further comprise an internal source capable of emitting the electromagnetic radiation.

Conveniently the method further comprises evaluating the statistics, in particular the frequency and/or intensity and/or photon number, of the electromagnetic radiation from the source based on the detected electromagnetic radiation.

Finally, conveniently the method further comprises identifying the identity of the chemical or biological agent based on the detected electromagnetic radiation.

The present invention is based on the unexpected conclusion that by way of using the phenomenon of surface plasmon resonance weak electromagnetic radiation/signals or signal changes can be enhanced and can be made (easier) detectable.

BRIEF DESCRIPTION OF THE DRAWINGS

Further features and advantages of the invention will become clear from the claims and following description, in which embodiments of the invention are illustrated in detail with reference to the schematic drawings:

DETAILED DESCRIPTION

Figure 1:
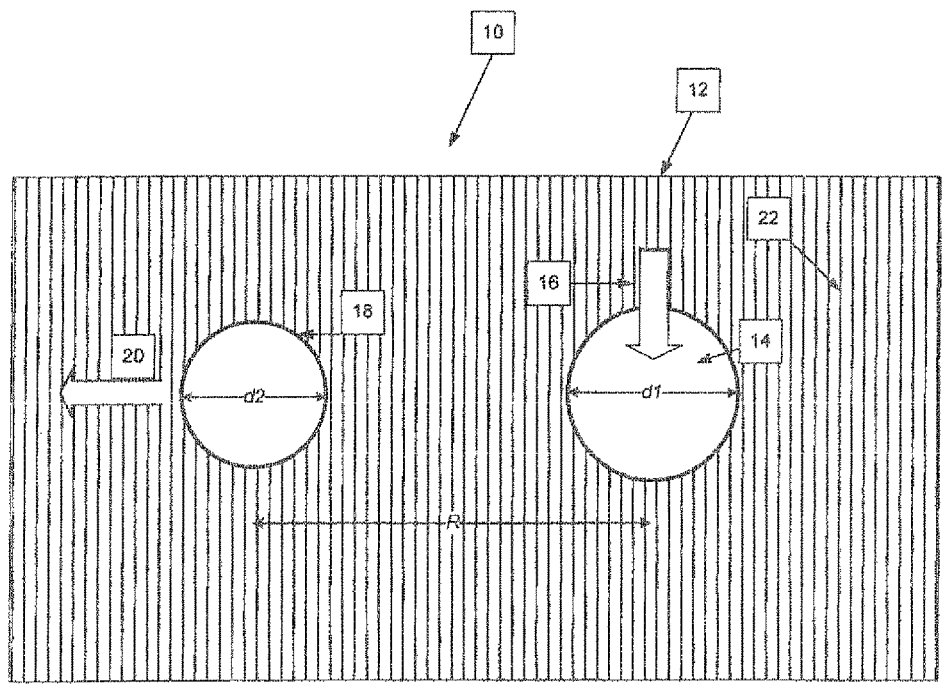
FIG. 1 shows a scheme of a system for sensing photons of electromagnetic radiation from an external source according to a first special embodiment of the invention.

The system 10 of FIG. 1 for sensing photons of electromagnetic radiation from an external source comprises a surface plasmon-based nanosensor 12. Said nanosensor 12 comprises a nanoparticle 14 of metal, e.g. silver or gold, or of semiconductor as a first element. The nanoparticle 14 is excitable to surface plasmon resonance, in particular localized as surface plasmon resonance, in the presence of electromagnetic radiation 16 from an external source (not shown). Furthermore, the nanosensor 12 comprises a quantum dot 18. A quantum dot is normally a nanometer sized semiconductor region within another material of larger Band-gap. In particular, the quantum dot 18 with diameter $d_2$ is situated in a distance of R to the nanoparticle 14 with the diameter $d_1$. The quantum dot 18 will be exciton-plasmon coupled to the nanoparticle 14 in the presence of the electromagnetic radiation 16 and will emit electromagnetic radiation 20 representative of the exciton-plasmon coupling.

The nanosensor 12 and the quantum dot 18 are embedded in PGB-material 22.

The system 10 further comprises a detector (not shown) for detecting the electromagnetic radiation 20 emitted by the quantum dot 18 in response to the electromagnetic radiation 16 from the external source (not shown). Also, said system 10 comprises an evaluation unit (not shown) for evaluating the statistics, in particular the frequency and/or the intensity and/or the photon number, of the electromagnetic radiation 16 from the external source (not shown). Preferably, the system 10 comprises a shielding (not shown) for shielding the quantum dot 18 against external electromagnetic radiation, in particular the external electromagnetic radiation 16.

By way of the nanosensor 12 and the system 10 photons—perhaps even single photons—can be detected within very narrow spectral width and provide statistical information about them, e.g. photon numbers. The PBG-material 22, e.g. silicon carbide, improves the preciseness of the detection of photons with certain frequency ranges. But the PBG-material is not a must. PBG-materials are characterized as having a gap in their dispersion relation characterized by an upper and lower energy band, corresponding to frequencies of light that are forbidden to propagate within the PBG-medium.

The system 10 can be described as made of a receiver or signal transformer, the quantum dot 18, situated near or close to the nanoparticle 14 that works as a photon collector. When photons of the electromagnetic radiation 16 from the external source (not shown) hit the nanoparticle 14, they excite certain plasmon modes that depend on the frequency of the photons and on the shape and material of the nanoparticle 14. These plasmons, in turn, generate a certain dipole moment, which, and through the near-field, will couple to the transformer (quantum dot 18), which will also generate a dipole moment that is proportional in magnitude to that of the nanoparticle 14 which in turn is proportional to the frequency and intensity of the incident electromagnetic radiation 16. The transformer (quantum dot 18) will transform the signal coming from the nanoparticle 14 into a more readable signal, e.g. electrical signal, through the population inversion that will occur within the transformer's (quantum dot) electronic states. This population difference carries within it the statistical properties of the incoming photons.

The usage of the PBG-material 22 has the effect of increasing the sensitivity of the nanoparticle 14 to the frequency of the incident electromagnetic radiation 16.

The system 10 can be used to detect specific signals, especially those close to the plasmon frequency of the nanoparticle 14 as these plasmons resonate, almost spontaneously, at their natural frequency leading to a large induced dipole moment in the nanoparticle 14 and consequently a stronger signal will be transmitted. In fact, the whole "system" can be tuned such that to resonate with very narrow frequency range. This can be done by designing the nanoparticle 14 and the quantum dot 18 such that they only resonate at a specific frequency, e.g. by choosing an elongated of spheroid nanoparticle for example instead of spherical.

Moreover, by changing the material and/or shape of the nanoparticle 14 it is possible to change its natural plasmonic frequency and consequently fine tune the "system" to be responsive to certain light frequencies, even if the intensity of the light is weak, as in electromagnetic signals emitted from for example some biological entities. The nanoparticle 14 can come in any shape, configuration and material.

The above configuration can be put in any other medium or configuration to produce the results desirable by the experimenter or manufacturer.

Even though in FIG. 1 spherical elements (nanoparticle 14 and quantum dot 18) are shown, this is not necessary. The elements can take any shape for getting the desired results. The nanoparticle 14 can have non-isomorphic shape that can support multiple plasmon resonances. Thus, by tuning the exciting element (nanoparticle) to these resonances, photons with different frequencies can be detected. It is also to be noted that ensembles of nanoparticles and/or quantum dots can be used.

A more readable signal is the usual electric signal that most electronics are using in their operations.

Every nanoparticle will have a specific plasmonic resonance frequency based on its shape and material and the surrounding material. The more the incoming/incident electromagnetic radiation, for example light, is in resonance with the plasmonic frequency, the more responsive the nanoparticle's electrons will be and the larger the dipole moment generated by the oscillations of the electrons will be. Consequently, the exciton plasmon coupling between the nanoparticle and the receiver, e.g. quantum dot 18, will be stronger. The outcome signal (electromagnetic radiation 20) from the quantum dot 18 depends on this coupling, labelled omega.

Thus, the coupling between the nanoparticle 14 and the quantum dot 18 depends on the dipole moments of the nanoparticle 14 and the quantum dot 18, which in turn depends on the frequency of the incident electromagnetic radiation 16. In addition, and as the below equation indicates, the signal lamda(p) coming out of the quantum dot 18 depends on the intensity of the electromagnetic radiation 16, which is proportional to the number of photons carried in the electromagnetic radiation 16. Thus, from the below equation, if lambda(p) is known, the other statistics of the electromagnetic radiation 16 (external field) can also be deduced.

$$\Lambda p = \frac{2}{1 - \sum_z} \times \left\{ \frac{4GKI}{\left[1 - \frac{2G}{\gamma Z_0} \sum_z\right]^2} + \gamma_2 Z_2 + \gamma_c \sum_z \right\}$$

Here, $\gamma_2$, $\gamma$ are the decay constant of the quantum dot 18 and nanoparticle 14, respectively, $\gamma_c = \gamma_2 Z_2^2 (2n_c + 1)$ and $n_c$ is the average number of quanta in the C-reservoir. $Z_0$ and $Z_2$ are the form constants of the nanoparticle 14 and the quantum dot 18, respectively, which are related to the PBG-material 22.

$$G = \frac{2\Omega}{\gamma_c}$$

with omega being the coupling constant of the quantum dot 18 and the nanoparticle 14 which depends on the relative values of their dipole moments $\mu_2$ and $\mu_0$. $\Sigma_z$ is the population inversion between the electronic states of the quantum dot 18.

$$K = \frac{4\mu_0^2}{\gamma Z_0^2 \hbar^2}$$

and I is the intensity of the field and is proportional to the number of photons.

The signal provided by the quantum dot 18 is an optical signal, because the electronic/electrons of the quantum dot 18 is/are excited to a higher state, when it de-excites, it will emit a photon/photons. It is up to the experimentalist or the manufacturer to decide what to do with this photon/these photons, for example keep it/them this way, amplifying it/them or turning it/them into an electronic signal, etc. It is the electromagnetic radiation 16 that pumps the nanoparticle 14 which in turn will excite a population inversion in the electronic states of the quantum dot 18 and consequently produces the final signal.

Figure 2:
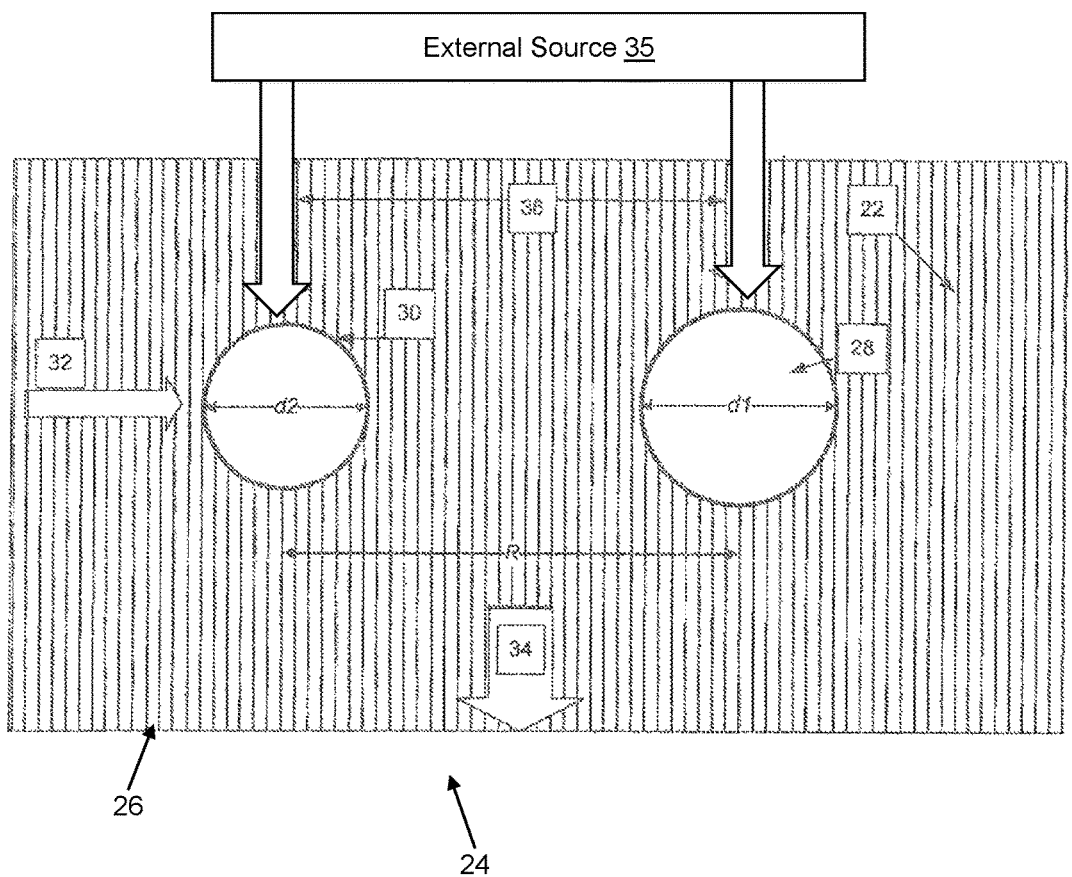
FIG. 2 shows a scheme of a system for sensing photons of electromagnetic radiation from an external source according to a second special embodiment of the invention.

FIG. 2 shows a further special embodiment of a system 24 for sensing photons of electromagnetic radiation from an external source (not shown). Said system 24 comprises a surface plasmon-based nanosensor 26. Said nanosensor 26 comprises a nanoparticle 28 of metal, preferably silver or gold, or of semiconductor, as a first element. Said nanoparticle 28 is excitable to surface plasmon resonance, in particular localized surface plasmon resonance, in the presence of electromagnetic radiation from a source. Furthermore, said nanosensor 26 comprises a quantum dot 30 as a second element for exciting surface plasmon resonance of the nanoparticle 28. In the present example, the diameter $d_1$ of the nanoparticle 28 is the same as the diameter $d_1$ of the nanoparticle 14, the diameter $d_2$ of the quantum dot 30 is the same as the diameter $d_2$ of the quantum dot 18 and the distance between the nanoparticle 28 and the quantum dot 30 is R and the same as the distance R between the nanoparticle 14 and the quantum dot 18. The nanoparticle 28 and the quantum dot 30 are totally embedded in PGB-material 22.

The system 24 further comprises a pumping unit for pumping the quantum dot 30 by way of electromagnetic radiation 32 and a detector (not shown) for detecting the total electromagnetic radiation 34 emitted by the nanoparticle 28 and the quantum dot 30 in response to electromagnetic radiation 36 emitted by an external source 35 and incident on the nanoparticle 28 and the quantum dot 30.

In addition, said system 24 further comprises an evaluation unit (not shown) for evaluating the statistics, in particular the frequency and/or the intensity and/or photon number, of the electromagnetic radiation 36 from the external source (not shown) based on the detected total electromagnetic radiation 34.

The configuration of the system 24 is similar to that of the system 10, with the exception, that in the system 24 the quantum dot 30 is pumped/excited by the electromagnetic radiation 32 and will pump the plasmons of the nanoparticle 28 which inturn will emit electromagnetic radiation, e.g. light, with certain statistics, frequency and spectral width. Applying the electromagnetic radiation 36 to the nanoparticle 28 and the quantum dot 30 will induce changes in the properties of the emitted total electromagnetic radiation, e.g. its intensity and spectral width. These changes are directly related to the properties of the electromagnetic radiation 36, e.g. intensity. Thus, from theses changes one can gain information on the applied electromagnetic radiation/external field.

Both the system 10 and the system 24 can be used to detect specific signals, especially those close to the plasmon frequency of the nanoparticle as these plasmons resonate, almost spontaneously, at their natural frequency leading to a large induced dipole moment in the nanoparticle and consequently a stronger signal will be transmitted.

For sensing photons with the system 24, the final total emitted signal/electromagnetic radiation 34 is read and information about the applied external field/electromagnetic radiation 36 is gathered from it.

Figure 3:
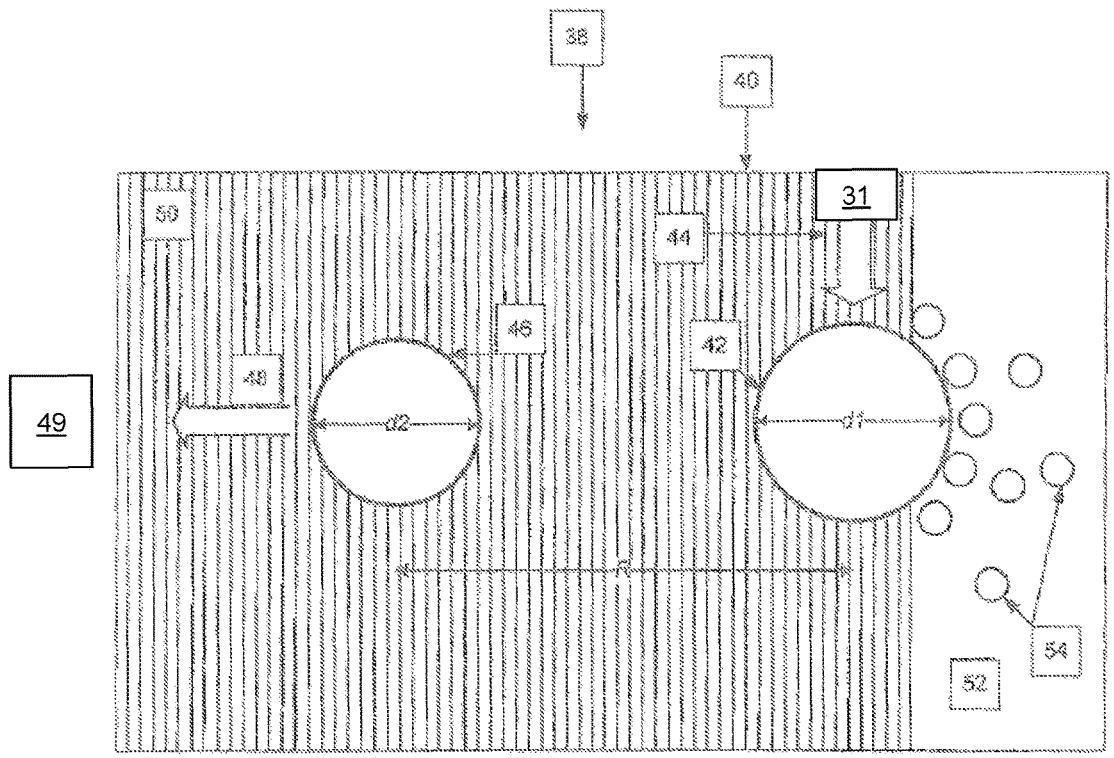
FIG. 3 shows a scheme of a system for sensing chemical or biological agents according to a first special embodiment of the invention.
Figure 4:
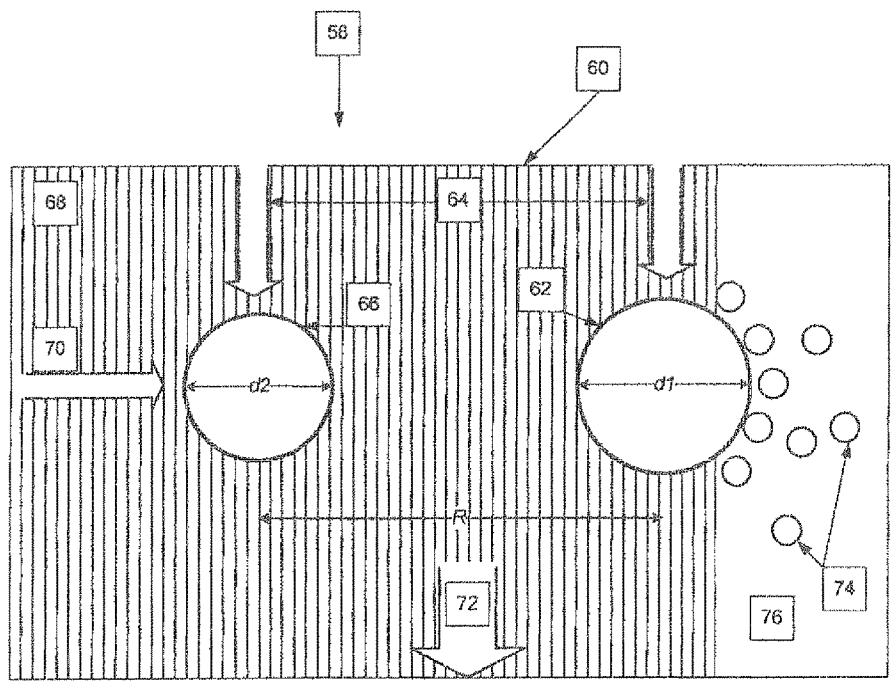
FIG. 4 shows a scheme of a system for sensing chemical or biological agents according to a second special embodiment of the invention.

FIGS. 3 and 4 show special embodiments of nanosensors and systems for sensing chemical or biological agents (analytes). Said systems are similar to the systems 10 and 24, respectively.

In particular, the system 38 comprises a surface plasmon-based nanosensor 40. Said nanosensor 40 comprises a nanoparticle 42 of metal, preferably silver or gold, or of semiconductor, as a first element. The nanoparticle 42 is excitable to surface plasmon resonance, in particular localized surface plasmon resonance, in the presence of electromagnetic radiation 44 from a source (not shown). In this example, said source might be external from the nanosensor 40 or inside the nanosensor 40. For example, the source may comprises a nanolaser 31 integrated with the first element 42 and the second element 46.

Furthermore, the nanosensor 40 comprises a quantum dot 46 near the nanoparticle 42 as a second element. Said quantum dot 46 will be exciton-plasmon coupled to the nanoparticle 42 in the presence of the electromagnetic radiation 44 and will emit electromagnetic radiation 48 representative of the exciton-plasmon coupling. In this example, the nanoparticle 42 and the quantum dot 46 have the same diameter $d_1$ and $d_2$, respectively, as the nanoparticle 14 and the quantum dot 18 of FIG. 1. The quantum dot 46 is also totally embedded in PGB-material 50.

However, the nanoparticle 42 is only partially embedded in the PGB-material 50. The nanoparticle 42 protudes a little bit from the PGB-material 50 into an external medium 52, e.g. buffer solution, thin film etc., where the chemical or biological agent (analyte) will be supplied. This is for enabling the nanoparticle 42 to sense the presence of the external agent 54. This protusion could effect the plasmonic resonance frequency of the nanoparticle 42 a bit or it may not. It depends on how much the nanoparticle 42 is protruding into the external medium 52. However, this can be easily accounted for by measuring the plasmon resonance prior to the inclusion of the external agent 54, and once the agent 54 is supplied, the actual shifting of the plasmon resonance can be measured.

The system 38 further comprises a detector 49 for detecting the electromagnetic radiation 48 emitted by the quantum dot 46 in response to the electromagnetic radiation 44 with said medium 52 or agent 54 in direct contact with the nanoparticle 42. In addition, said system 38 further comprises an evaluation unit (not shown) for evaluating the identity of the chemical or biological agent 54 based on the detected electromagnetic radiation 56.

One idea behind the plasmonic bio nanosensor 40 and the system 38 is that the resonance of the plasmons is greatly sensitive to the surrounding environment. In fact, the surface plasmon resonance frequency depends specifically on the dielectric function of the plasmonic material, e.g. gold and silver, and the surrounding material, e.g. silicon, buffer solution, thin film, etc.

Now when working as a bio-detector, what happens is that when the biological or chemical agents get into close proximity to the surface of the nanoparticle 42, either they will change the permittivity of the surrounding material (external medium 52), e.g. a buffer solution, or stick to the surface of the nanoparticle 42. In either case they will change the surrounding conditions of the nanoparticle 42, which in turn will change the resonance frequency of the surface plasmons, shifting them toward for example the red or blue end of the spectrum depending on the changes induced by the biological or chemical external agent 54. This shifting can be detected and based upon it can determine the identity of the external agent 54. In the system 38 the external agent 54 will change the surface plasmon resonance frequency of the nanoparticle 42 and consequently will change how the nanoparticle 42 will interact with the electromagnetic radiation 48, which will translate into a change in the signal output of the quantum dot 46. From this change, one can deduce information about the external agent 54. It should be noted that the quantum dot 46 should be shielded from the external agent 54 to ensure that they will not interfere with the signal coming out of the quantum dot 46. Otherwise, this interference should be included in the final calculations.

The system 58 shown in FIG. 4 comprises a surface plasmon-based nanosensor 60. Said nanosensor 60 comprises a nanoparticle 62 of metal, preferably silver or gold, or of semiconductor, as a first element. The nanoparticle 62 is excitable to surface plasmon resonance, in particular localized surface plasmon resonance, in the presence of electromagnetic radiation 64 from an external or internal source (not shown). Further, said nanosensor 60 comprises a quantum dot 66 as a second element near the nanoparticle 62 for exciting surface plasmon resonance of the nanoparticle 62. The nanoparticle 62 and the quantum dot 66 have the same diameter $d_1$ and $d_2$, respectively, and are spaced apart by a distance R as the nanoparticle 42 and the quantum dot 46 of the system 38. The quantum dot 66 is totally embedded in a PGB-material 68, whereas the nanoparticle 62 is only partially embedded in said PGB-material 68 like the nanoparticle 42 of the system 38.

The system 58 further comprises a pumping unit (not shown) for pumping the quantum dot 66 by means of electromagnetic radiation 70 and a detector (not shown) for detecting the total electromagnetic radiation 72 emitted by the nanoparticle 62 and the quantum dot 66. Also, said system 58 comprises an evaluation unit (not shown) for evaluating the identity of the chemical or biological agent 74 (in an external medium 76) based on the detected electromagnetic radiation 72.

In the system 58 of FIG. 4, just like in the system 38 of FIG. 3, the changes induced by the external agent 74 will translate into changes in the total electromagnetic radiation 72. In fact, on said system 58, and when working as a bio-detector, the external agent 74 will shift the plasmon resonance of the nanoparticle 62. This shift will be detected from the statistics of the total electromagnetic radiation, e.g. light, emitted out of the system 58, which was generated from the interaction between the pumped quantum dot 66 and the nanoparticle 62. In addition, as in the case of the system 38, it might be much better if the quantum dot 66 is shielded from the external agent 74.

The nanosensor 60 as well the system 58 are simple, small and mobile. Like in the system 38 of FIG. 3, in the system 58 of FIG. 4 and integrated source of electromagnetic radiation, e.g. light, like a nanolaser 31 could be incorporated.

One important factor that determines the efficiency of the nanosensor is how accurate it is. Plasmonic resonances are fairly narrow. However, the spectrum of the electromagnetic radiation, for example light, emitted from the system is usually not narrow due to broadening processes. This could be overcome by the PGB-material 68. Incorporating the PGB-material into the system will greatly narrow the spectrum of the electromagnetic radiation, e.g. light, emitted from the system, rendering the sensing operation much more sensitive and accurate. However, an ensemble of anyone of the systems described above may be necessary to ensure better detecting.

The features disclosed in the foregoing description, in the claims and/or in the accompanying drawings may, both separately and in any combination thereof, be material for realising the invention in diverse forms thereof.

REFERENCE LIST 10 system
12 nanosensor
14 nanoparticle
16 electromagnetic radiation
18 quantum dot
20 electromagnetic radiation
22 PGB-material
24 system
30 quantum dot
26 nanosensor
28 nanoparticle
32 electromagnetic radiation
34 total electromagnetic radiation
36 electromagnetic radiation
38 system
40 nanosensor
42 nanoparticle
44 electromagnetic radiation
46 quantum dot
48 electromagnetic radiation
50 PGB-material
52 external medium
54 agent
58 system
60 nanosensor
62 nanoparticle
64 electromagnetic radiation
66 quantum dot
68 PGB-material
70 electromagnetic radiation
72 total electromagnetic radiation
74 agent
76 external medium
$d_1$ diameter of nanoparticle 14, 28, 62
$d_2$ diameter of quantum dots 18, 30, 66
R distance

The invention claimed is:

1. A nanosensor comprising:
   a nanolaser,
   at least one first material of metal or of semiconductor, and
   at least one second material;
   wherein the at least one first material has plasmon resonance in the presence of electromagnetic radiation, and
   wherein the at least one second material is:
      coupled to the at least one first material through near-field interaction, and
      configured to emit electromagnetic radiation representative of exciton-plasmon coupling to the first material, wherein the electromagnetic radiation emitted by the at least one second material has a spectral width;
   wherein the nanolaser is integrated with and is unique from the at least one first material and the at least one second material; and
   wherein the at least one second material is totally embedded in a matrix of Photonic or Polaritonic Band-gap (PGB)-material and/or wherein the at least one first material is at least partially embedded in a matrix of Photonic or Polaritonic Band-gap (PGB)-material.

2. The nanosensor according to claim 1, wherein the at least one first material is a nanoparticle and/or the at least one second material is a quantum dot.

3. A system for sensing chemical agent or biological agent, comprising:
   the nanosensor according to claim 1, and
   a detector configured to detect the electromagnetic radiation emitted from the nanosensor and detect the changes in exciton plasmon coupling due to the interaction between the chemical agent or biological agent and the nanosensor.

* * * * *